United States Patent
Hancock et al.

(10) Patent No.: US 11,446,083 B2
(45) Date of Patent: Sep. 20, 2022

(54) MICROWAVE AMPLIFIER

(71) Applicant: Creo Medical Limited, Chepstow (GB)

(72) Inventors: Christopher Paul Hancock, Bath (GB); Christopher Duff, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 275 days.

(21) Appl. No.: 16/959,063

(22) PCT Filed: Apr. 26, 2019

(86) PCT No.: PCT/EP2019/060720
§ 371 (c)(1),
(2) Date: Jun. 29, 2020

(87) PCT Pub. No.: WO2019/207098
PCT Pub. Date: Oct. 31, 2019

(65) Prior Publication Data
US 2020/0397506 A1    Dec. 24, 2020

(30) Foreign Application Priority Data

Apr. 27, 2018 (GB) ..................................... 1806940

(51) Int. Cl.
*H03F 3/191* (2006.01)
*A61B 18/18* (2006.01)
(Continued)

(52) U.S. Cl.
CPC ........... *A61B 18/1815* (2013.01); *H03F 1/56* (2013.01); *H03F 3/19* (2013.01);
(Continued)

(58) Field of Classification Search
CPC ....................................................... H03F 3/191
(Continued)

(56) References Cited

U.S. PATENT DOCUMENTS 5,410,281 A * 4/1995 Blum .................. H01P 5/16
                                                        333/127
6,757,523 B2 * 6/2004 Fry ..................... H04B 1/48
                                                        455/73
(Continued)

FOREIGN PATENT DOCUMENTS

GB      2551339 A     12/2017
JP   2013009031 A      1/2013

OTHER PUBLICATIONS

Fu, W., et al., "High efficiency GaN E power amplifier at 5.8GHz with harmonic control network", IEEE Wireless Power Transfer Conference (WPTC), ISBN 978-1-4799-2923-8, pp. 205-207, (2014).

(Continued)

*Primary Examiner* — Henry Choe
(74) *Attorney, Agent, or Firm* — ArentFox Schiff LLP

(57) ABSTRACT

A microwave amplifier having a load network which provides more efficient amplification of a low power microwave frequency signal. The amplifier comprises a transistor and a load network coupled to the transistor output to shape a waveform of an amplified microwave signal at the transistor current source plane. The load network comprises: a fundamental matching network to provide impedance matching at a fundamental frequency; a half-wave transmission line for a second harmonic frequency disposed between the transistor output and the fundamental matching network; a quarter-wave stub and a five-quarter-wave stub for a third harmonic frequency arranged on the half-wave transmission line to provide an open circuit condition at the third harmonic; and a quarter-wave stub for the second harmonic frequency and a quarter-wave stub for the fundamental frequency, arranged on the half-wave transmission line to provide a short circuit condition at the second harmonic frequency.

15 Claims, 3 Drawing Sheets

(51) Int. Cl.
 *H03F 1/56* (2006.01)
 *H03F 3/19* (2006.01)
 *A61B 18/00* (2006.01)
(52) U.S. Cl.
 CPC .............. *A61B 2018/00577* (2013.01); *A61B 2018/00982* (2013.01); *A61B 2018/1823* (2013.01); *A61B 2018/1861* (2013.01); *H03F 2200/387* (2013.01); *H03F 2200/423* (2013.01)
(58) Field of Classification Search
 USPC ....................................... 330/302, 305, 306
 See application file for complete search history.

(56) References Cited

U.S. PATENT DOCUMENTS 11,146,215 B2 * 10/2021 Wang ........................ H03F 1/56
2013/0267943 A1 10/2013 Hancock

OTHER PUBLICATIONS

International Search Report and the Written Opinion issued by the International Searching Authority in corresponding International Patent Application No. PCT/EP2019/060720, dated Aug. 16, 2019.
Raemer, A. et al., "Software optimization of a supply modulated GaN-amplifier for baseband access ET systems", German, IEEE, ISBN: 978-1-4577-2096-3, pp. 1-4, Mar. 12, 2012.
Search Report issued by the United Kingdom Patent Office in corresponding British Patent Application No. 1806940.01, dated Oct. 23, 2018.

* cited by examiner

MICROWAVE AMPLIFIER

CROSS-REFERENCE TO RELATED APPLICATIONS

This application is a National Stage entry of International Application No. PCT/EP2019/060720, filed on Apr. 26, 2019, which claims priority to British Patent Application No. 1806940.1, filed on Apr. 27, 2018. The disclosures of the priority applications are hereby incorporated in their entirety by reference.

FIELD OF THE INVENTION

The invention relates to microwave amplifiers. In particular it relates to a microwave amplifier configuration for use with an electrosurgical device for treating biological tissue with microwave energy.

BACKGROUND TO THE INVENTION

The use of microwave energy in the treatment of biological tissue through electrosurgery is well known. However, it remains a challenge to deliver microwave energy in a closely controlled manner, primarily due to the effect of losses between the microwave source and an applicator structure which is in contact with the biological tissue to be treated. These effects can be particularly problematic in minimally invasive procedures which make use of surgical scoping devices such as endoscopes. Surgical scoping devices typically comprise a body from which an instrument cord extends. An applicator structure is inserted into a patient's body through an instrument channel which is a lumen extending through the length of the instrument cord. Delivering microwave energy to the applicator therefore requires transmitting this energy through the instrument cord.

In order to be able to treat biological tissue, large amounts of energy need to be delivered by the applicator. This means that high power signals must be transmitted through the instrument cord. However, transmitting high power signals results in large losses, which can lead to undesirable endoluminal heating which can have a negative effect on the body. Overcoming these issues usually requires that lower power signals are transmitted through the instrument cord, which leads to longer treatment times. Longer treatment times reduces patient comfort and may also prolong recovery time after surgery.

SUMMARY OF THE INVENTION

At its most general, the present invention is a microwave amplifier having a load network which provides more efficient amplification of a low power microwave frequency signal. The microwave amplifier of the present invention is particularly suited for use with an electrosurgical apparatus for the treatment of biological tissue, for example ablation, resection, coagulation etc.

The increased efficiency resulting from an output load network according to the present invention allows the microwave amplifier and/or generator to be located at any point between a DC power source and a microwave applicator structure for delivering energy to tissue. A smaller, more efficient amplifier has lower power requirements and also a reduced need for cooling. For example, in some embodiments the amplifier and/or microwave generator may be incorporated into a handle of an electrosurgical apparatus, or within the applicator structure itself. The present invention also allows the manufacture of a portable generator unit for use with an electrosurgical apparatus.

According to a first aspect of the present invention, there is provided microwave amplifier for amplifying electromagnetic (EM) signals at a fundamental frequency, the amplifier comprising: a transistor configured to provide an amplified microwave signal at an output thereof; and a load network coupled to the output for shaping a waveform of the amplified microwave signal at the transistor current source plane, wherein the load network comprises: a fundamental matching network that is tunable to provide impedance matching at the fundamental frequency; a half-wave transmission line for a second harmonic frequency of the amplified microwave signal, the half-wave transmission line being disposed between the output and the fundamental matching network; a quarter-wave stub and a five-quarter-wave stub for a third harmonic frequency of the amplified microwave signal arranged on the half-wave transmission line to provide an open circuit condition at the third harmonic frequency; and a quarter-wave stub for the second harmonic frequency and a quarter-wave stub for the fundamental frequency, arranged on the half-wave transmission line to provide a short circuit condition at the second harmonic frequency. For example, the amplifier may be an integrated circuit based amplifier.

With this configuration, the fundamental matching network can operate independently of the waveform shaping effect provided by the rest of the load network. Put another way, the stubs that provide the waveform shaping effect are configured in the invention to counteract or inhibit any effect on the fundamental frequency to which the fundamental matching network is matched. This may allow the fundamental matching network to be pre-configured, e.g. before connection to the transistor. On assembling the amplifier, the load network can be optimised (e.g. tuned) to achieve the required waveform shaping effect through appropriate placement of the stubs without affecting the impedance match at the fundamental frequency provided by the fundamental matching network.

This independence is achieved in particular through the use of the five-quarter-wave stub for the third harmonic frequency. This stub removes the effect of the quarter-wave stub for the third harmonic frequency on the fundamental and second harmonic matching.

Independent tuning is particularly useful as amplifier transistors are commonly supplied as part of a package, and not as individual components. Tuning of the load network can be highly dependent on the characteristics of the package, but these characteristics are rarely given by manufacturers or suppliers. As a result, it is often necessary to tune the load network for a particular transistor package. In the present invention, this can be done without affecting the impedance match of the load network at the fundamental frequency, making it possible to design and tune part of the load and matching network before precise characteristics of a transistor package are known. Furthermore, if the possible impact of the harmonic tuning network, i.e. the waveform shaping part of the load network, upon the stability of the amplifier is unknown due to a lack of transistor information, a less efficient class of amplifier (for example class B) may be designed and built before characteristics of the package are known, and a higher efficiency amplifier, with reduced conduction angle modes, such as class F, produced and tested experimentally 'on the bench' with the transistor package in place.

The amplifier of the present invention is a class F microwave amplifier. By terminating odd harmonics in open circuit terminations and terminating even harmonics in short circuit terminations, high amplifier efficiencies are achieved with a square wave voltage waveform and half sinusoidal wave current waveform at the transistor current source plane, or output. In particular it has been found that the present invention provides high efficiencies of at least 80% while considering only up to the third harmonic of the fundamental frequency in the load network. This level of efficiency is sufficient for use in a microwave generator line-up of an electrosurgical apparatus as described below. In some embodiments, the load network may comprise additional terminations for higher-order harmonic frequencies in order to achieve higher efficiencies. Theoretically, efficiencies approaching 100% can be achieved if a sufficient number of higher-order harmonics are terminated by the load network.

Preferably the quarter-wave stub and the five-quarter wave stub for the third harmonic frequency are arranged to oppose each other at a distance along the half-wave transmission line equal to a quarter-wave from the transistor current source plane for a third harmonic frequency. This ensures proper open circuit termination of the third harmonic frequency. The ability to tune the load network independently of a fundamental matching network accounts for the unknown electrical length between the intrinsic transistor current source plane and the package external plane, that is, the electrical distance between the transistor output and the output of the package within which the transistor is provided. In some embodiments, the half-wave transmission line for the second harmonic frequency comprises a quarter-wave transmission line for a third harmonic frequency (including the internal package drain connection electrical length), and so the quarter-wave stub and five-quarter-wave stub for the third harmonic frequency may be arranged to oppose each other at the output of the quarter-wave transmission line for the third harmonic frequency.

Preferably, the quarter-wave stub for the second harmonic frequency and the quarter-wave stub for the fundamental frequency are arranged to oppose each other at an output of the half-wave transmission line. This ensures proper closed circuit termination of the second harmonic frequency.

Optionally, a bias voltage may be applied to the transistor through the quarter-wave stub for the fundamental frequency. Preferably a shunt capacitor to ground is also arranged at the connection of the bias voltage input and the quarter-wave stub for the fundamental frequency. The capacitor may provide a sufficiently low reactance to approximate a short circuit at microwave frequencies.

According to a second aspect of the present invention, there is provided a microwave signal generator for generating high power microwave electromagnetic (EM) radiation, the generator comprising: a microwave generator arranged to generate microwave EM radiation at a first power, and a microwave amplifier which may be an amplifier according to the first aspect of the present invention. The microwave amplifier is arranged to amplify the microwave EM radiation from the first power to a second power that is higher than the first power. By using a microwave amplifier as described above, the present invention allows the manufacture of easily portable microwave signal generators which are capable of producing high power microwave EM radiation. The high efficiency apparatus may be smaller and have reduced power and cooling requirements. A portable generator may be desirable, for example, for use with an electrosurgical haemostatic device, especially a device which may be used in emergency situations. The microwave signal generator may comprise a direct current (DC) power source for supplying DC energy, which may be required by the microwave generator. The DC power supply may be in the form of a battery, in particular a removable battery. In this way, a portable generator may be provided which provides sufficient energy for haemostasis and coagulation in which the power supply can easily be replaced if further energy delivery is required.

According to a third aspect of the present invention, there is provided an electrosurgical apparatus for performing electrosurgery, the apparatus comprising: a microwave signal generator arranged to generate microwave electromagnetic (EM) radiation at a first power; a microwave amplifier according to the first aspect of the invention, arranged to amplify the microwave EM radiation from a first power to a second power that is higher than the first power; a probe arranged to deliver the microwave EM radiation at the second power from a distal end thereof for treating biological tissue; and a feed structure for conveying microwave EM energy; wherein the probe is arranged at a distal end of the feed structure, and the microwave signal generator and the microwave amplifier are distributed along the feed structure.

By providing an electrosurgical apparatus in this way, using a microwave amplifier as described above with respect to the first aspect, high power microwaves for electrosurgery can be produced while reducing losses throughout the feed structure and avoiding problems which stem from endoluminal heating.

The present invention allows the microwave amplifier to be located closer to, or even integrated with, the probe, reducing losses normally arising through transmission of high power microwave EM energy to the probe. This has numerous advantages, such as allowing reduced diameter cables to be used, in turn allowing electrosurgery in places which would otherwise be difficult to reach. Reduced losses also means reduced heating of a transmission cable forming the feed structure.

The present invention also ensures reduced power requirements for the amplifier, so there may also be reduced losses and power dissipation throughout the feed structure leading to the microwave amplifier.

In some embodiments, the microwave signal generator may also be integrated with the probe. Microwave power losses and associated drawbacks present in known devices, as described above, can therefore be further avoided or reduced. The apparatus may further comprise a direct current (DC) power source for supplying DC energy to the microwave signal generator, wherein the DC power source is also integrated with the probe. In this way, microwave generation may be carried out entirely within the probe, and in some embodiments no external power source is required.

In some embodiments, the electrosurgical apparatus may comprise a scoping device having a body and an instrument cord, wherein an instrument channel extends through the instrument cord and the probe is insertable through the instrument channel. For example, the scoping device may be an endoscope, gastroscope, laparoscope or the like. The microwave signal generator may be integrated with the body of the scoping device in order to provide a portable electrosurgical apparatus having the advantages of the present invention. In some embodiments, a DC power source may be integrated with the body of the scoping device.

Optionally, the electrosurgical apparatus may comprise a handle, which may be connected to the probe via a flexible shaft. Preferably, the flexible shaft is insertable through the instrument channel of a scoping device. The microwave signal generator may be integrated with the handle. In some embodiments, a DC power source may be integrated with the handle.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz.

Similarly, references to a "conductor" or "conductive" material herein are to be interpreted as meaning electrically conductive unless the context makes clear that another meaning is intended.

BRIEF DESCRIPTION OF THE DRAWINGS

Examples embodying the invention are discussed in detail below with reference to the accompanying drawings, in which.

DETAILED DESCRIPTION

Figure 1:
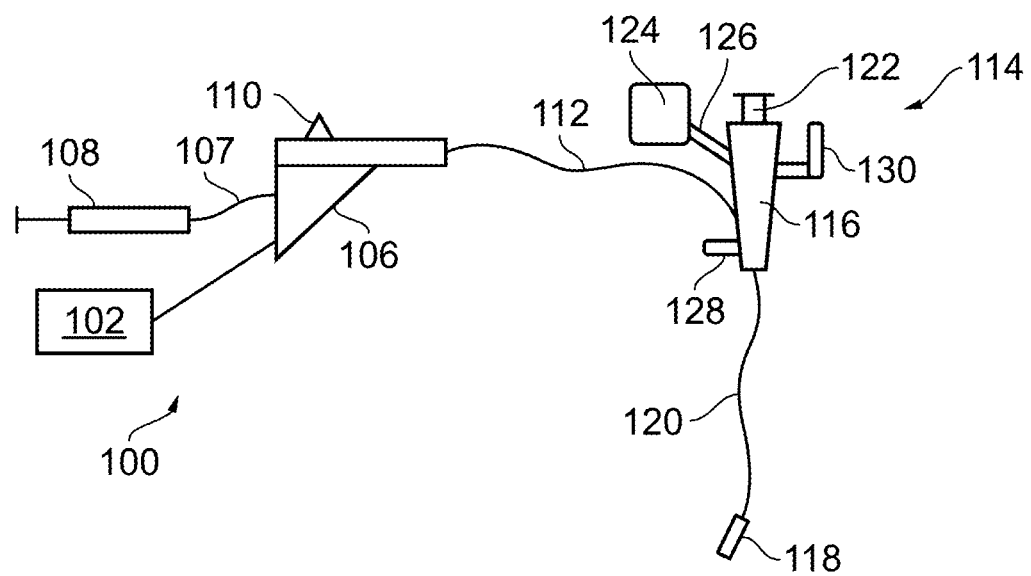
FIG. 1 is a schematic view of a complete electrosurgical apparatus in which the present invention is applied.

FIG. 1 is a schematic diagram of a complete electrosurgical apparatus 100 in which the present invention may be used.

The apparatus comprises a surgical scoping device 114, such as an endoscope, gastroscope, laparoscope or the like. The surgical scoping device 114 comprises a body 116 having a number of input ports and an output port from which an instrument cord 120 extends. The instrument cord 120 comprises an outer jacket which surrounds a plurality of lumens. The plurality of lumens convey various things from the body 116 to a distal end of the instrument cord 120. One of the plurality of lumens is an instrument (working) channel. A flexible shaft 112 is insertable along the entire length of the instrument (working) channel. Other lumens may include a channel for conveying optical radiation, e.g. to provide illumination at the distal end or to gather images from the distal end. The body 116 may include an eye piece 122 for viewing the distal end. In order to provide illumination at the distal end, a light source 124 (e.g. LED or the like) may be connected to the body 116 by an illumination input port 126.

At a proximal end of the flexible shaft 112 there is a handle 106, which may be connected to receive a fluid supply 107 from a fluid delivery device 108, such as a syringe, although this need not be essential. If needed, the handle 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the handle to provide full control.

The apparatus 100 may also comprise a generator 102 for supplying microwave frequency and, optionally, radiofrequency (RF) electromagnetic (EM) energy to a distal assembly 118. In some embodiments, the generator 102 is configured as a DC power source to supply only DC energy. The generator 102 is connected to the handle 106 by an interface cable.

At a distal end of the flexible shaft 112, there is a distal end assembly, or applicator, 118 (not drawn to scale in FIG. 1) that is shaped to pass through the instrument channel of the surgical scoping device 114 and protrude (e.g. inside the patient) at the distal end of the instrument cord 120. The distal end assembly includes an active tip for delivering microwave energy into biological tissue, as discussed in more detail below.

The structure of the distal assembly 118 may be arranged to have a maximum outer diameter equal to or less than 2.0 mm, e.g. less than 1.9 mm (and more preferably less than 1.5 mm) and the length of the flexible shaft can be equal to or greater than 1.2 m.

In some embodiments, the body 116 may include a DC power source 128 that is connected to delivery DC energy to the distal end assembly 118 along the flexible shaft, e.g. using suitable leads. In other embodiments, the DC power source may be provided in place of the generator 102. The DC power source 128 or 102 may be a battery (e.g. a lithium ion battery), supercapacitor or a fuel cell, which may be mounted in the body 116. In another example, the DC power source 128 or 102 may be a coupling unit arranged to inductively or magnetically couple energy into the device from a remote source (not shown). In this case, the coupling unit may comprise internal rectification and filtering to obtain a DC signal from coupled energy.

In yet further examples, the DC power source may be part of the distal end assembly 118, in which case leads extending along the instrument channel are not required.

It may be desirable to control the position of at least the distal end of the instrument cord 120. The body 116 may include a control actuator 130 that is mechanically coupled to the distal end of the instrument cord 120 by one or more control wires (not shown), which extend through the instrument cord 120. The control wires may travel within the instrument channel or within their own dedicated channels. The control actuator 130 may be a lever or rotatable knob, or any other known catheter manipulation device. The manipulation of the instrument cord 120 may be software-assisted, e.g. using a virtual three-dimensional map assembled from computer tomography (CT) images.

Figure 2:
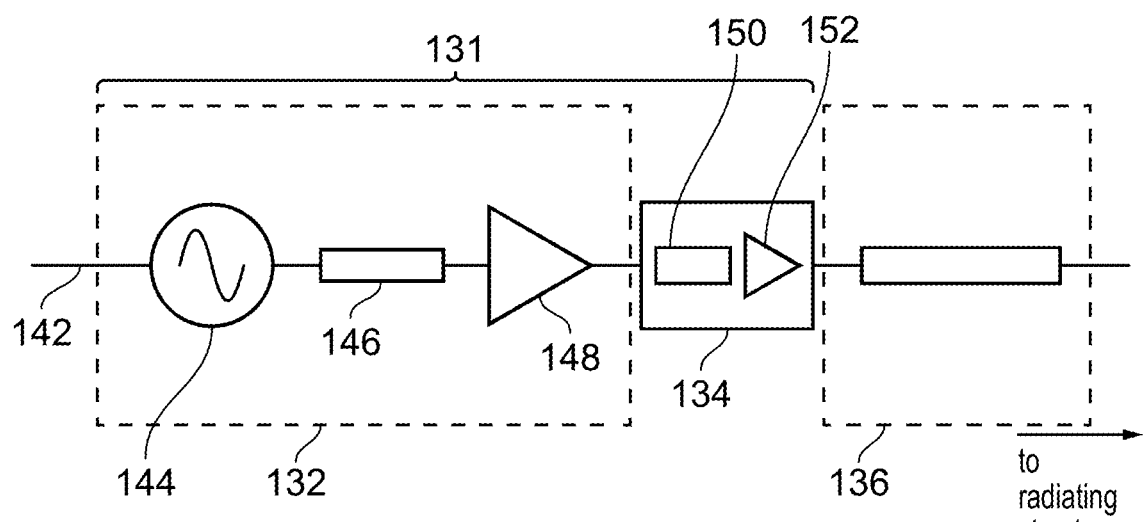
FIG. 2 is a schematic view of a microwave generator line up.

FIG. 2 is a schematic view showing components of a microwave generator line up 131. The microwave generator line up 131 includes generator circuitry 132 for producing a low power microwave signal, and an output stage 134 for amplifying the signal to a level suitable for electrosurgery, e.g. ablation treatment of biological tissue.

The generator circuitry 132 comprises an oscillator 144 for outputting a microwave signal, e.g. having a frequency of 1 GHz or more, preferably 5.8 GHz or more. The oscillator 144 may be a voltage controlled oscillator (VCO) or a dielectric resonator oscillator (DRO). The oscillator 144 may receive DC power as an input. DC power may be provided by the generator 102 or by the DC power source 128. The output from the oscillator 144 may be pulsed by a modulator 146. The output from the oscillator 144 is provided to a driver amplifier 148, which is arranged to generate an input signal for the output stage 134. The driver amplifier 148 may be any suitable MMIC device. The line up 131 may further include an attenuator (not shown) to provide control over the amplitude of the signal delivered to the output stage 134. The output stage 134 itself may comprise a biasing circuit 150 and a GaN-based transistor 152 configured as a power amplifier. The output stage may include circuitry (not shown) to protect the output stage components from signal reflects back from the radiating structure. For example, a circulator may be mounted on a forward path from the GaN-based transistor. The circulator may divert reflected power to a dump load. However, this protection structure is not essential because GaN-based structures can be robust enough to cope. The output stage 134 also includes a load network, as described below.

Components of the microwave generator line up 131 may be positioned within different parts of the electrosurgical apparatus 100. In some embodiments, the generator line up 131, including both the generator circuitry 132 and output stage 134, may form part of a microwave generator 102. By using a microwave amplifier according to the present invention, the microwave generator 102 may be easily portable. Alternatively, the oscillator 144 and modulation switch 146 may be part of the distal end assembly 118, which may be desirable to significantly reduce losses associated with passing microwave signals through cables. Optionally, the oscillator 144 and modulation switch 146 may be located in or at the body 116 of the surgical scoping device, and the output stage located in the applicator 118, reducing losses as only low-power microwave signals need to be transmitted along the instrument channel. In another example, the whole generator circuitry 132 (i.e. including the driver amplifier 148) may be located at a proximal distance from the distal end assembly, e.g. in the body 116. Thus, the input signal for the output stage 134 may be transmitted along the instrument channel.

To illustrate, one example may comprise a DRO with an output power of 10 dBm (10 mW) and a MMIC with a gain of 20 dB located in the body of the scoping device. Even if the insertion loss of the cable is 10 dB in this scenario, there would still be 20 dBm (100 mW) available at the distal end assembly. In this example, the output stage may comprise a second MMIC followed by the GaN-based transistor 152. If the second MMIC has a gain of 10 dB and a high density GaN device a gain of 10 dB, then there will be 40 dBm (10 W) available for delivery.

The transmission line 136 may be any suitable structure for conveying the microwave power generated by the output stage 134 to the radiating structure. For example, both coaxial (including waveguide) structures and microstrip structures may be used, as explained in more detail below.

Figure 3:
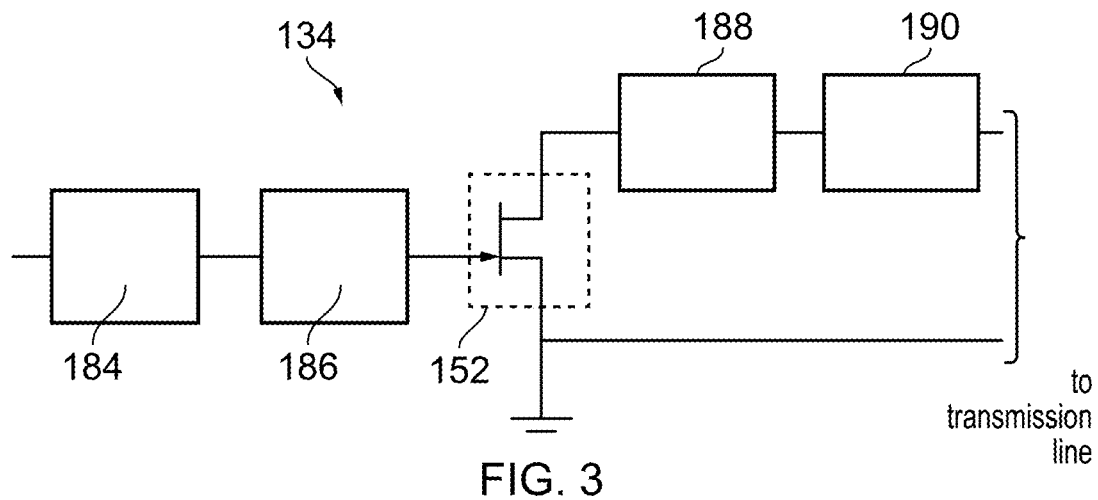
FIG. 3 is a schematic view of components in an output stage which may be used with the present invention.

FIG. 3 is a schematic diagram of the components in an output stage 134 that can be used in an embodiment of the invention. The output stage 134 uses a high density GaN-based HEMT as an amplifier for an input received from the generator circuitry 132. Whilst any suitable amplifier configuration may be used, in accordance with the present invention it is most desirable to bias the output transistor using a class F structure. This configuration allows the device to take the power added efficiency (PAE) close to its theoretical limit. In particular, the structure shown in FIG. 3 may be able to achieve a PAE of at least 80%, or up to 90%. It is these high efficiencies resulting from the form of the output stage 134 which allows components of the microwave generator line up 131 to be separated and spread across components of the electrosurgical apparatus 100, as only lower power microwave signals are required to be sent to the output stage 134, resulting in smaller losses when the signal is passed through cables. High efficiencies also allow for construction of a microwave generator 102 which is portable.

The class F structure in FIG. 3 provides a load network at an output of the HEMT 152 amplifier, the load network comprising a matching circuit 188 and a resonant circuit 190. A first resonant circuit (e.g. a LC or tank circuit) 184 is also provided at an input to the GaN-based HEMT 152 with a respective matching circuit 186 (e.g. a series LC circuit).

The load network, made of the output resonant circuit 188 and matching network 190 together, is a harmonic termination network, which is explained below. The device is biased near or at cut-off, in a similar manner to class B operation.

In order to increase the efficiency in terms of the amount of microwave power produced at the output to DC and input microwave signal at the input, it is desirable to operate the GaN device using a scheme other than the standard linear Class A scheme, i.e. Class B, AB, C, D, E or F.

The efficiency of an amplifier is limited by the characteristics of the transistors used in the design. If class F design is used then it is theoretically possible to achieve 100% efficiency, but this assumes that the transistor is an ideal current source. In practice, it should be possible to achieve at least 70% power added efficiency (PAE) using a class F arrangement.

A class F amplifier has as its base a class B amplifier, with the component transistor being biased between the amplifier's knee and transconductance regions rather than purely in the transconductance region. This biasing results in clipping of the current and voltage output waveforms, i.e. the sinusoid output waveforms are distorted, and waveform engineering can be performed by selecting an appropriate load or harmonic termination network for the output of the amplifying transistor.

For example, the second resonant circuit 190 may be configured to shape the output waveform based on the load appearing as a short circuit to even harmonics (i.e. short circuit at $2f_1$, where $f_1$ is the fundamental resonant frequency of the circuit) and as an open circuit to odd harmonics (i.e. open circuit at $3f_1$). Accordingly, the drain voltage waveform is shaped towards a square wave whereas the drain current is shaped such that it resembles a half-wave sinusoidal waveform, dependent upon the number of harmonics controlled. Note that for the $n^{th}$ harmonic, $f_n = nf_1$ and $\lambda_n = \lambda_1/n$. Higher-order harmonics can be accounted for, but result in diminishing returns in terms of PAE. A resonant circuit which accounts for the second and third harmonics is sufficient to achieve at least 80% efficiency, and so represents a good balance of efficiency and load network complexity/cost. By accounting for only the second and third harmonics, the load network may be made small enough to be provided as part of an integrated circuit. For example, an integrated circuit based amplifier may be integrated in the probe itself.

The first resonant circuit 184 assists in ensuring that the device is driven by square wave pulses. The first resonant circuit 184 may thereby introduce harmonic generation and allow simpler current sources to be used. In some embodiments, the first resonant circuit 184 is not required and an input waveform is sinusoidal.

Figure 4:
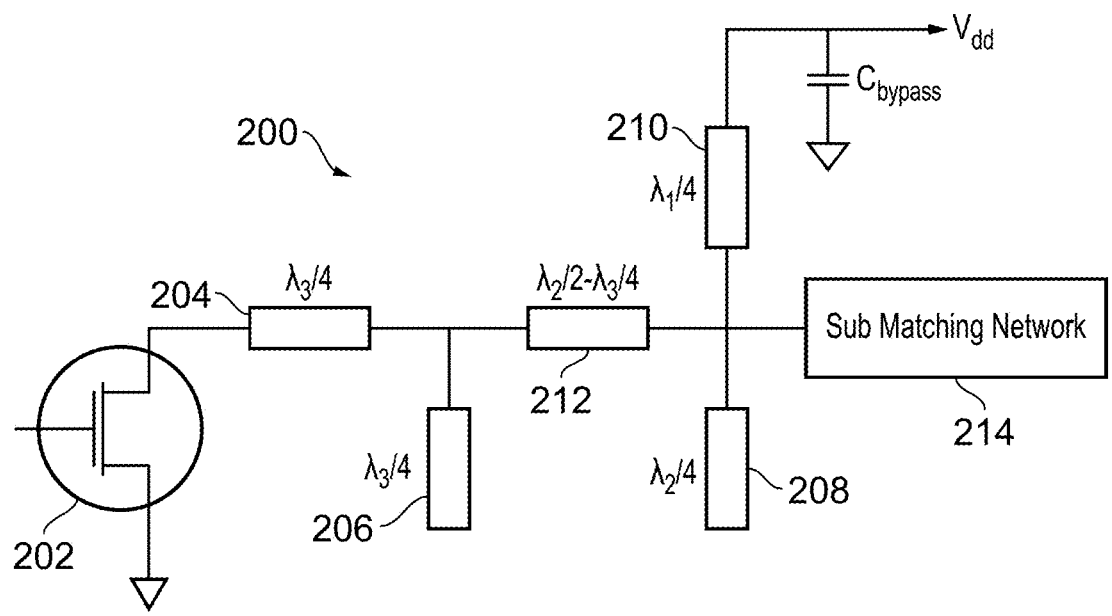
FIG. 4 shows a prior art load network.

An example of a known load or harmonic termination network 200 for the output of a transistor 202 is shown in FIG. 4. The load network 200 comprises a half-wave transmission line for the second harmonic frequency (i.e. $\lambda_2/2$ transmission line), formed from a quarter-wave transmission line 204 for the third harmonic frequency—a $\lambda_3/4$ transmission line 204—and a $\lambda_2/2 - \lambda_3/4$ transmission line 212 connected in series. The $\lambda_3/4$ transmission line 204 length includes the transmission line internal to the package of the transistor leading to the drain output connection, the characteristics of which may be unknown.

A quarter-wave stub 206 for the third harmonic frequency (a $\lambda_3/4$ stub) is arranged at the output of the quarter-wave transmission line 204 in order to provide an open circuit to the intrinsic transistor drain at the third harmonic frequency. Due to the relationship between the harmonic and resonant frequencies, it should be noted that $\lambda_3/4=\lambda_1/12$, and so the quarter-wave stub for the third harmonic frequency may also be considered a $\lambda_1/12$ stub.

To provide a short circuit at the second harmonic frequency $f_2$, the load network 200 comprises a quarter-wave stub 208 for the second harmonic frequency (a $\lambda_2/4$ stub), arranged opposite a quarter-wave stub 210 for the fundamental frequency (a $\lambda_1/4$ stub). These are arranged at the output of the effective half-wave transmission line for the second harmonic.

A bias voltage, $V_{dd}$, of the transistor is applied through the quarter-wave stub 210 for the fundamental frequency. This ensures that the bias feed is spaced a half-wavelength distance at the second harmonic frequency from the transistor 202 in order to provide the correct impedance at the second harmonic.

A sub matching network 214 is also provided, and can be tuned to provide impedance matching at the fundamental frequency, $f_1$, while taking the rest of the circuit 200 into account. The sub matching network 214, similarly to the rest of the load network 200, may comprise a further arrangement of transmission lines and stubs, and a DC blocking capacitor may also be present.

However, tuning of the load network 200 to increase the efficiency of the amplifier affects the requirements for the sub matching network 214. Designing and tuning a sub matching network 214 which is also adversely affected by the rest of the load network can be difficult and time consuming, and may lead to sub-optimal results. A network in accordance with the present invention overcomes these difficulties, as explained below.

Figure 5:
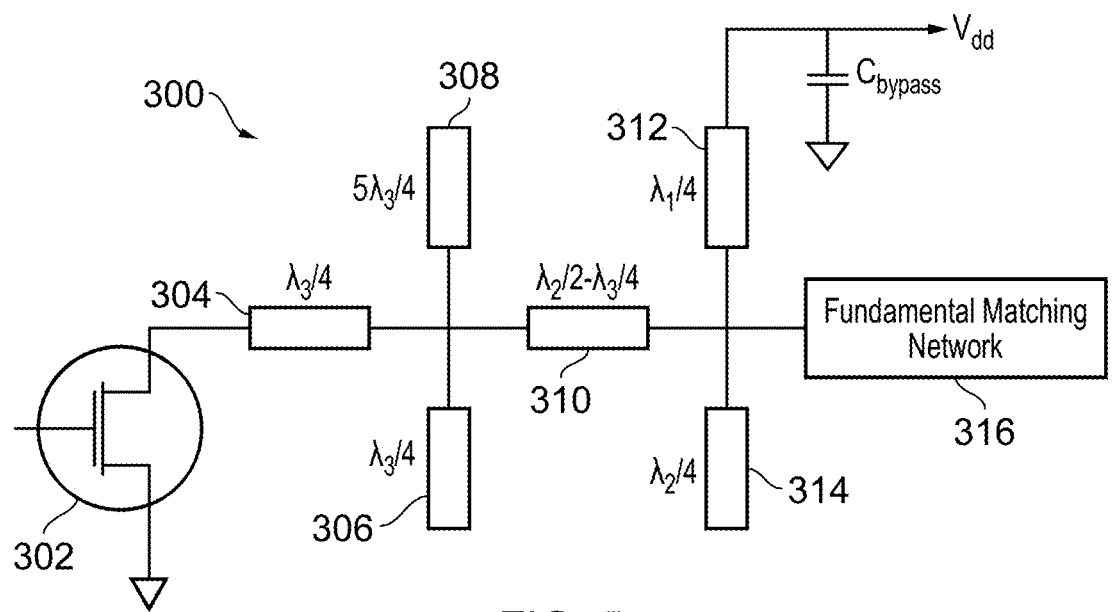
FIG. 5 shows a load network in accordance with the present invention.

FIG. 5 shows a schematic diagram of a load network 300 in accordance with the present invention.

The load network 300 is coupled to the output of a transistor 302 which is arranged to amplify microwave signals delivered to the transistor 302 at a fundamental frequency, $f_1$. The load network 300 comprises a half-wave transmission line for the second harmonic frequency, formed from a quarter-wave transmission line 304 for the third harmonic frequency (a $\lambda_3/4$ transmission line) and a $\lambda_2/2$-$\lambda_3/4$ transmission line 310 connected in series. The $\lambda_3/4$ transmission line 304 length includes the transmission line internal to the package of the transistor leading to the drain output connection, the characteristics of which may be unknown.

A quarter-wave stub 306 and a five-quarter-wave stub 308 for the third harmonic frequency (a $\lambda_3/4$ stub 306 and a $5\lambda_3/4$ stub 308, respectively) are arranged opposite each other on the effective half-wave transmission line. They are positioned away from the transistor 302, specifically the intrinsic transistor 302 current source, at a distance equal to a quarter-wave for a third harmonic frequency, i.e. at the output of the quarter-wave transmission line 304. The quarter-wave stub 306 provides an open circuit at the third harmonic frequency, while the five-quarter-wave stub 308 reinforces the open circuit at the third harmonic frequency, while also counteracting the effect the quarter-wave stub 306 has on the load network 300 at the second harmonic and fundamental frequencies.

At the output of the effective half-wave transmission line, i.e. the output of the $\lambda_2/2$-$\lambda_3/4$ transmission line 310, are arranged a quarter-wave stub 314 at the second harmonic frequency and a quarter-wave stub 312 at the fundamental frequency. These stubs provide a short circuit at the second harmonic frequency.

Figure 6:
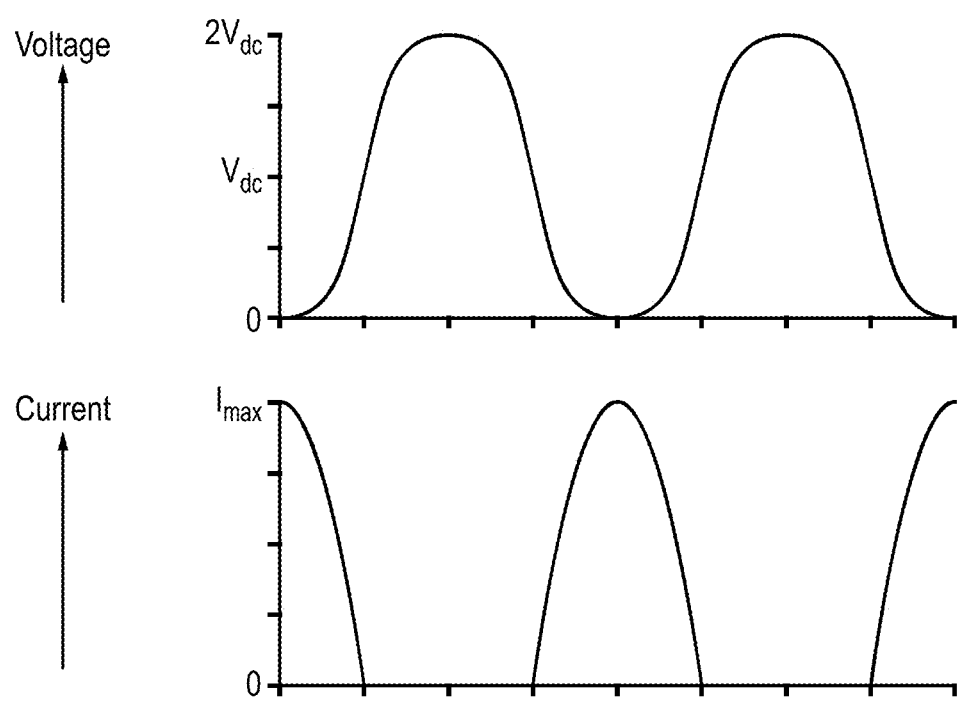
FIG. 6 shows a graph of output voltage and current for an amplifier according to the present invention.

By providing a short circuit at the second harmonic frequency and an open circuit at the third harmonic frequency, the load network 300 produces an approximately square wave voltage output and a half-sinusoid current output, as shown in FIG. 6 as a function of time. This ensures that the amplifier operates at a high efficiency of at least 80%.

A bias voltage, $V_{dd}$, of the transistor is applied through the quarter-wave stub 312 for the fundamental frequency. The quarter-wave stub 312 in combination with the microwave capacitor $C_{bypass}$ presents an open circuit at the fundamental frequency, and so have no effect on the rest of the network 300. At the second harmonic frequency, the quarter-wave stub 312 and capacitor present a short circuit, reinforcing the effect of the quarter-wave stub 314 at the second harmonic frequency.

Transistors are typically available only as part of a package and not as individual components. Information regarding the package itself is usually limited, which introduces difficulties in designing a load network. For example, it is often necessary to know the exact distance between the transistor output, i.e. the intrinsic current generator plane, and other components to form transmission lines of the correct length. For this reason, it is valuable to be able to tune a load network for an amplifier with the transistor package in place, rather than relying only on a hypothetical model.

The load network of the present invention allows tuning of the matching network 316 and of the remainder of load network 300 to be carried out independently. The fundamental matching network 316 can be tuned to match impedance at the fundamental frequency without being affected by tuning of the remainder of the load network. This is due to the addition and positioning of the five-quarter-wave stub 308 for the third harmonic frequency, which removes the effect of quarter-wave stub 306 on the fundamental and second harmonic matching while also reinforcing an open circuit for the third harmonic frequency.

In this way, the intermediate portion of the load network 300 and fundamental matching network 316 can in combination enable the device to operate as a Class F amplifier, in which the tuning to match to the relevant harmonics can be performed by the intermediate portion independently of the tuning to the fundamental performed by the fundamental matching network 316.

The fundamental matching network 316 may be designed and tuned for a specific transistor 302 or transistor package. This can be done in advance, and then mounted in the load network 300 configuration of the invention. The intermediate portion can then be tuned to enable the Class F operation without affecting the tuning of the fundamental matching network.

The fundamental matching network 316 may comprise a further arrangement of transmission lines and stubs, and a DC blocking capacitor may also be present. The fundamental matching network 316 may be optimised for matching at the fundamental frequency during a design phase using a model of the transistor 302, taking into account the effective half-wave transmission line for the second harmonic.

By using a microwave amplifier according to the present invention, very high amplifier efficiencies can be achieved. As a result of these high efficiencies a microwave generator for an electrosurgical device can be made which is smaller and more readily portable than known generators.

In addition, some embodiments of the present invention envisage that the microwave generator or microwave amplifier may be located within another section of the electrosurgical apparatus, such as within a handle or a radiating structure. In these embodiments, high amplifier efficiencies mean that DC or microwave frequency signals can be transmitted to the microwave generator or amplifier at a lower power. This results in less power dissipation, and makes cooling of the apparatus easier to implement.

The invention claimed is:

1. A microwave amplifier for amplifying electromagnetic (EM) signals at a fundamental frequency, the amplifier comprising:
a transistor configured to provide an amplified microwave signal at an output thereof; and
a load network coupled to the output for shaping a waveform of the amplified microwave signal,
wherein the load network comprises:
a fundamental matching network that is tunable to provide impedance matching at the fundamental frequency;
a half-wave transmission line for a second harmonic frequency of the amplified microwave signal, the half-wave transmission line being disposed between the output and the fundamental matching network;
a quarter-wave stub and a five-quarter-wave stub for a third harmonic frequency of the amplified microwave signal arranged on the half-wave transmission line to provide an open circuit condition at the third harmonic frequency; and
a quarter-wave stub for the second harmonic frequency and a quarter-wave stub for the fundamental frequency, arranged on the half-wave transmission line to provide a short circuit condition at the second harmonic frequency.

2. A microwave amplifier according to claim 1, wherein the quarter-wave stub and the five-quarter wave stub for the third harmonic frequency are arranged to oppose each other at a distance along the half-wave transmission line equal to a quarter-wave for a third harmonic frequency.

3. A microwave amplifier according to claim 1, wherein the quarter-wave stub for the second harmonic frequency and the quarter-wave stub for the fundamental frequency are arranged to oppose each other at an output of the half-wave transmission line.

4. A microwave amplifier according to claim 1, wherein a bias voltage is applied to the transistor through the quarter-wave stub for the fundamental frequency.

5. A microwave amplifier according to claim 4, further comprising a capacitor arranged between the bias voltage input and the quarter-wave stub for the fundamental frequency.

6. A microwave amplifier according to claim 1, wherein the half-wave transmission line for the second harmonic frequency comprises a quarter-wave transmission line for a third harmonic frequency, the quarter-wave stub and five-quarter-wave stub for the third harmonic frequency being arranged to oppose each other at the output of the quarter-wave transmission line for the third harmonic frequency.

7. A microwave amplifier according to claim 1, wherein the transistor is a GaN-based HEMT.

8. A microwave signal generator for generating high power microwave electromagnetic (EM) radiation, the generator comprising:
a microwave source arranged to generate microwave EM radiation at a first power, and
a microwave amplifier according to claim 1, wherein the microwave amplifier is arranged to amplify the microwave EM radiation from the first power to a second power that is higher than the first power.

9. A microwave signal generator according to claim 8, further comprising a direct current (DC) power source for supplying DC energy.

10. An electrosurgical apparatus for performing electrosurgery, the apparatus comprising:
a microwave source arranged to generate microwave electromagnetic (EM) radiation at a first power;
a microwave amplifier according to any claim 1, arranged to amplify the microwave EM radiation from a first power to a second power that is higher than the first power;
a probe arranged to deliver the microwave EM radiation at the second power from a distal end thereof for treating biological tissue; and
a feed structure for conveying microwave EM energy from the microwave generator to the microwave amplifier and to the probe,
wherein the probe is arranged at a distal end of the feed structure.

11. An electrosurgical apparatus according to claim 10, further comprising a direct current (DC) power source for supplying DC energy to the microwave signal generator, wherein the DC power source is integrated with the probe.

12. An electrosurgical apparatus according to claim 10, wherein the microwave amplifier is mounted in the probe.

13. An electrosurgical apparatus according to claim 10, wherein the microwave signal generator is mounted in the probe.

14. An electrosurgical apparatus according to claim 10, wherein the apparatus further comprises a scoping device having a body and an instrument cord, wherein an instrument channel extends through the instrument cord, and wherein the probe is insertable through the instrument channel.

15. An electrosurgical apparatus according to claim 10, wherein the apparatus further comprises a handle connected to the probe via a flexible shaft.

* * * * *